(12) United States Patent
Zhao et al.

(10) Patent No.: US 10,820,837 B2
(45) Date of Patent: Nov. 3, 2020

(54) SYSTEM AND METHOD FOR ANGLE MEASUREMENTS USING MAGNETIC RESONANCE IMAGES

(71) Applicant: Siemens Healthcare GmbH, Erlangen (DE)

(72) Inventors: Liang Zhao, Shanghai (CN); Esther Raithel, Dormitz (DE); Yiqiang Zhan, West Chester, PA (US)

(73) Assignee: Siemens Healthcare GmbH, Erlangen (DE)

( * ) Notice: Subject to any disclaimer, the term of this patent is extended or adjusted under 35 U.S.C. 154(b) by 56 days.

(21) Appl. No.: 16/379,122

(22) Filed: Apr. 9, 2019

(65) Prior Publication Data

US 2019/0307366 A1    Oct. 10, 2019

Related U.S. Application Data

(60) Provisional application No. 62/654,689, filed on Apr. 9, 2018.

(51) Int. Cl.
*A61B 5/107* (2006.01)
*A61B 5/055* (2006.01)
(Continued)

(52) U.S. Cl.
CPC ............ *A61B 5/1071* (2013.01); *A61B 5/055* (2013.01); *A61B 5/4571* (2013.01);
(Continued)

(58) Field of Classification Search
CPC ..... A61B 5/1071; A61B 5/055; A61B 5/4571; A61B 5/7278; A61B 2576/02; G06T 7/11;
(Continued)

(56) References Cited

U.S. PATENT DOCUMENTS

| | | | |
|---|---|---|---|
| 2013/0083984 A1* | 4/2013 | Chabanas | G06T 19/00 382/128 |
| 2016/0235381 A1* | 8/2016 | Scanlan | G16H 30/20 |

(Continued)

OTHER PUBLICATIONS

Xia Y, Fripp J, Chandra SS, Walker D, Crozier S, Engstrom C: "Automated 3D quantitative assessment and measurement of alpha angles from the femoral head-neck junction using MR imaging", Phys Med Biol. Oct. 7, 2015;60 (19):7601-16; 2015.

(Continued)

*Primary Examiner* — David F Dunphy
(74) *Attorney, Agent, or Firm* — Schiff Hardin LLP (57) ABSTRACT

In a method for alpha angle measurements of a bone joint based on magnetic resonance imaging (MRI) data of the bone joint, a three-dimensional (3D) bone surface image of the bone joint is generated based on two-dimensional (2D) segmentations on radial plane slices of the bone joint. Based on the 3D bone surface image, a head center of a head of the bone joint and a neck axis of a neck of the bone joint are estimated. An alpha angle model is constructed based on the estimated head center and neck axis. Further, the alpha angle measurement is determined for each of the radial plane slices of the bone joint based on the constructed alpha angle model.

20 Claims, 7 Drawing Sheets
(4 of 7 Drawing Sheet(s) Filed in Color)

(51) Int. Cl.
*A61B 5/00* (2006.01)
*G06T 7/00* (2017.01)
*G06T 17/10* (2006.01)
*G06T 7/11* (2017.01)

(52) U.S. Cl.
CPC .......... *A61B 5/7278* (2013.01); *G06T 7/0012* (2013.01); *G06T 7/11* (2017.01); *G06T 17/10* (2013.01); *A61B 2576/02* (2013.01); *G06T 2207/10088* (2013.01); *G06T 2207/20084* (2013.01); *G06T 2207/30008* (2013.01)

(58) Field of Classification Search
CPC .................. G06T 7/0012; G06T 17/10; G06T 2207/10088; G06T 2207/20084; G06T 2207/30008
See application file for complete search history.

(56) References Cited

U.S. PATENT DOCUMENTS

| | | | | |
|---|---|---|---|---|
| 2018/0140309 A1* | 5/2018 | Fouts | ................ | A61B 17/1703 |
| 2018/0146953 A1* | 5/2018 | Jaremko | ................ | A61B 8/483 |
| 2019/0298452 A1* | 10/2019 | Veilleux | ................ | G16H 30/20 |

OTHER PUBLICATIONS

Nötzli HP, Wyss TF, Stoecklin CH et-al. "The contour of the femoral head-neck junction as a predictor for the risk of anterior impingement", J Bone Joint Surg Br. 2002;84 (4): 556-60.; 2002.

\* cited by examiner

SYSTEM AND METHOD FOR ANGLE MEASUREMENTS USING MAGNETIC RESONANCE IMAGES

CROSS-REFERENCE TO RELATED APPLICATIONS

The present application claims the benefit of the filing date of provisional application 62/654,689, filed on Apr. 9, 2018, the contents of which are incorporated herein by reference in their entirety.

TECHNICAL FIELD

The present invention concerns methods and devices for anatomical angle measurements using magnetic resonance imaging (MRI), and in particular to such methods and devices for alpha angle measurements of magnetic resonance (MR) images.

BACKGROUND

MRI is a modality that mainly delivers qualitative images and the demand for quantitative outcomes is growing. In musculoskeletal (MSK) applications, anatomical angle measurements may be used to quantify relations between parts of a joint and compare those with normal values. The alpha angle in the hip joint is an example of such anatomical relevant angles that may be used to quantify joint function, e.g., femoroacetabular impingement (FAI). FAI is one cause of the hip joint developing osteoarthrosis and an abnormal alpha angle is considered as an indicator for FAI or the risk of FAI.

In conventional systems and methods, the intra- and inter-reader variability of the alpha angle is very high. Such variability may be caused by the measurement of the angle being in only a single plane, and that the measured angle is highly dependent on the choice of the plane. Further, the Alpha angle depends on landmarks that are not very distinctive to the human eye. For example, radiologists conventionally measure the alpha angle manually as described in the paper by HP Notzli, et al., "The contour of the femoral head-neck junction as a predictor for the risk of anterior impingement."

Although providing an alpha angle on each slice of a radial slice group has the potential to better describe the three-dimensional (3D) morphology of the joint, such process is time extensive while note reducing the variability. For example, the paper by Xia et al., "Automated 3D quantitative assessment and measurement of alpha angles from the femoral head-neck junction using MR imaging," describes a similar automated process, that disadvantageously requires a time-consuming shape-model based 3D segmentation of bones and employs an inflexible smoothness constraint for computing the alpha angles.

SUMMARY

An object of the present disclosure is to provide anatomical angle measurements (e.g. alpha angle measurements) using magnetic resonance imaging (MRI) that advantageously provides an efficient and accurate alpha angle measurement (e.g. of a femur). Aspects include a fast landmark detection-based approach to generate a radial slice group, and the segmentation on 2D radial slices to improve algorithmic performance. The segmentation can leverage one or more deep learning technologies in one or more aspects. For example, the methods and devices can use deep or machine learning to perform alpha angle measurements automatically. The MR images can be images of joints, such as a hip/femoral joint, but is not limited thereto.

Cam lesion severity may be assessed using a two-dimensional (2D) alpha angle, which may be used as an indicator (e.g. a value exceeding 50°) of femoral head asphericity and irregularity of the femoral head-neck (FHN) junction.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The exemplary embodiments of the present disclosure will be described with reference to the accompanying drawings.

DETAILED DESCRIPTION

Figure 1:
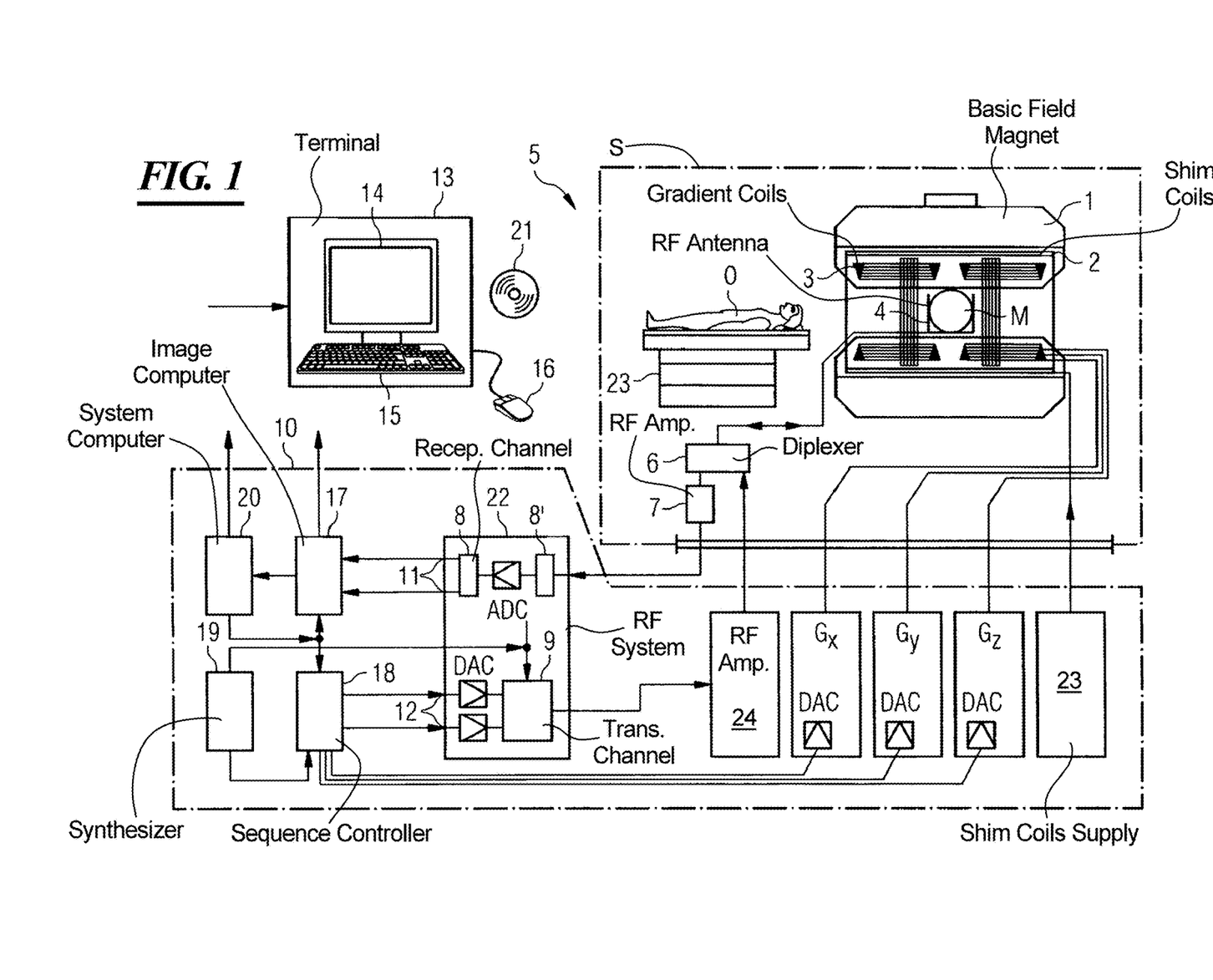
FIG. 1 is a block diagram of a magnetic resonance apparatus constructed and operating in accordance with an exemplary embodiment of the present disclosure.

FIG. 1 schematically illustrates a magnetic resonance apparatus 5 (a magnetic resonance imaging or tomography device). A basic field magnet 1 generates, a temporally constant strong magnetic field for the polarization or alignment of the nuclear spin in a region of an examination subject O, such as a portion of a human body that is to be examined, lying on a table 23 in order to be moved into the magnetic resonance apparatus 5. The high degree of homogeneity in the basic magnetic field necessary for the magnetic resonance measurement (data acquisition) is defined in a typically sphere-shaped measurement volume M, in which the portion of the human body that is to be examined is placed. In order to support the homogeneity requirements temporally constant effects are eliminated by shim-plates made of ferromagnetic materials are placed at appropriate positions. Temporally variable effects are eliminated by shim-coils 2 and an appropriate controller 23 for the shim-coils 2.

A cylindrically shaped gradient coil system 3 is incorporated in the basic field magnet 1, composed of three windings. Each winding is supplied by a corresponding amplifier Gx, Gy and Gz, with power for generating a linear gradient field in a respective axis of a Cartesian coordinate system. The first partial winding of the gradient field system 3 generates a gradient Gx in the x-axis, the second partial winding generates a gradient Gy in the y-axis, and the third partial winding generates a gradient Gz in the z-axis. Each amplifier 24-26 has a digital-analog converter (DAC), controlled by a sequencer 18 for the accurately-times generation of gradient pulses.

A radio-frequency antenna 4 is located within the gradient field system 3, which converts the radio-frequency pulses provided by a radio-frequency power amplifier 24 into a magnetic alternating field for the excitation of the nuclei by tipping ("flipping") the spins in the subject or the region thereof to be examined, from the alignment produced by the basic magnetic field. The radio-frequency antenna 4 is composed of one or more RF transmitting coils and one or more RF receiving coils in the form of an annular, linear or matrix type configuration of coils. The alternating field based on the precessing nuclear spin, i.e. the nuclear spin echo signal normally produced from a pulse sequence composed of one or more radio-frequency pulses and one or more gradient pulses, is also converted by the RF receiving coils of the radio-frequency antenna 4 into a voltage (measurement signal), which is transmitted to a radio-frequency system 22 via an amplifier 7 of a radio-frequency receiver channel 8, 8'. The radio-frequency system 22 furthermore has a transmitting channel 9, in which the radio-frequency pulses for the excitation of the magnetic nuclear resonance are generated. For this purpose, the respective radio-frequency pulses are digitally depicted in the sequencer 18 as a series of complex numbers, based on a given pulse sequence provided by the system computer 20. This number series is sent via an input 12, in each case, as real and imaginary number components to a digital-analog converter (DAC) in the radio-frequency system 22 and from there to the transmitting channel 9. The pulse sequences are modulated in the transmitting channel 9 to a radio-frequency carrier signal, the base frequency of which corresponds to the resonance frequency of the nuclear spin in the measurement volume. The modulated pulse sequences of the RF transmitter coil are transmitted to the radio-frequency antenna 4 via an amplifier 28.

Switching from transmitting to receiving operation occurs via a transmission-receiving switch 6. The RF transmitting coil of the radio-frequency antenna 4 radiates the radio-frequency pulse for the excitation of the nuclear spin in the measurement volume M and scans the resulting echo signals via the RF receiving coils. The corresponding magnetic resonance signals obtained thereby are demodulated to an intermediate frequency in a phase sensitive manner in a first demodulator 8' of the receiving channel of the radio-frequency system 22, and digitalized in an analog-digital converter (ADC). This signal is then demodulated to the base frequency. The demodulation to the base frequency and the separation into real and imaginary parts occurs after digitization in the spatial domain in a second demodulator 8, which emits the demodulated data via outputs 11 to an image processor 17. In an image processor 17, an MR image is reconstructed from the measurement data obtained in this manner, which includes computation of at least one disturbance matrix and the inversion thereof, in the image processor 17. The management of the measurement data, the image data, and the control program occurs via the system computer 20. The sequencer 18 controls the generation of the desired pulse sequences and the corresponding scanning of k-space with control programs. The sequencer 18 controls accurately-timed switching (activation) of the gradients, the transmission of the radio-frequency pulse with a defined phase amplitude, and the reception of the magnetic resonance signals. The time base for the radio-frequency system 22 and the sequencer 18 is provided by a synthesizer 19. The selection of appropriate control programs for the generation of an MR image, which are stored on a memory or other recording medium, for example, on a DVD 21 or other memory, as well as other user inputs such as a desired number n of adjacent clusters, which are to collectively cover the desired k-space, and the display of the generated MR images, occurs via a terminal 13, which includes one or more input interfaces for enabling input entries, such as, e.g. a keyboard 15, and/or a mouse 16, and one or more output interfaces for enabling a display 14, such as, e.g. a display screen. The components within the dot-dash outline 10 are commonly called a magnetic resonance scanner. The components within the dot-dash outline 10 may collectively be referred to as the magnetic resonance controller.

Thus, the magnetic resonance apparatus 5 as shown in FIG. 1 may include various components to facilitate the measurement, collection, and storage of MRI image data and/or MRI phase data. This MRI image and/or phase data may then be utilized in accordance with the exemplary angular measurements processes and systems of the embodiments of the present disclosure. The MRI image and/or phase data may be processed using one or more deep learning technologies, convolutional neural networks, or similar machine learning algorithms to determine calculate one or more alpha angles or other anatomical angles as would be understood by one of ordinary skill in the art.

Figure 2:
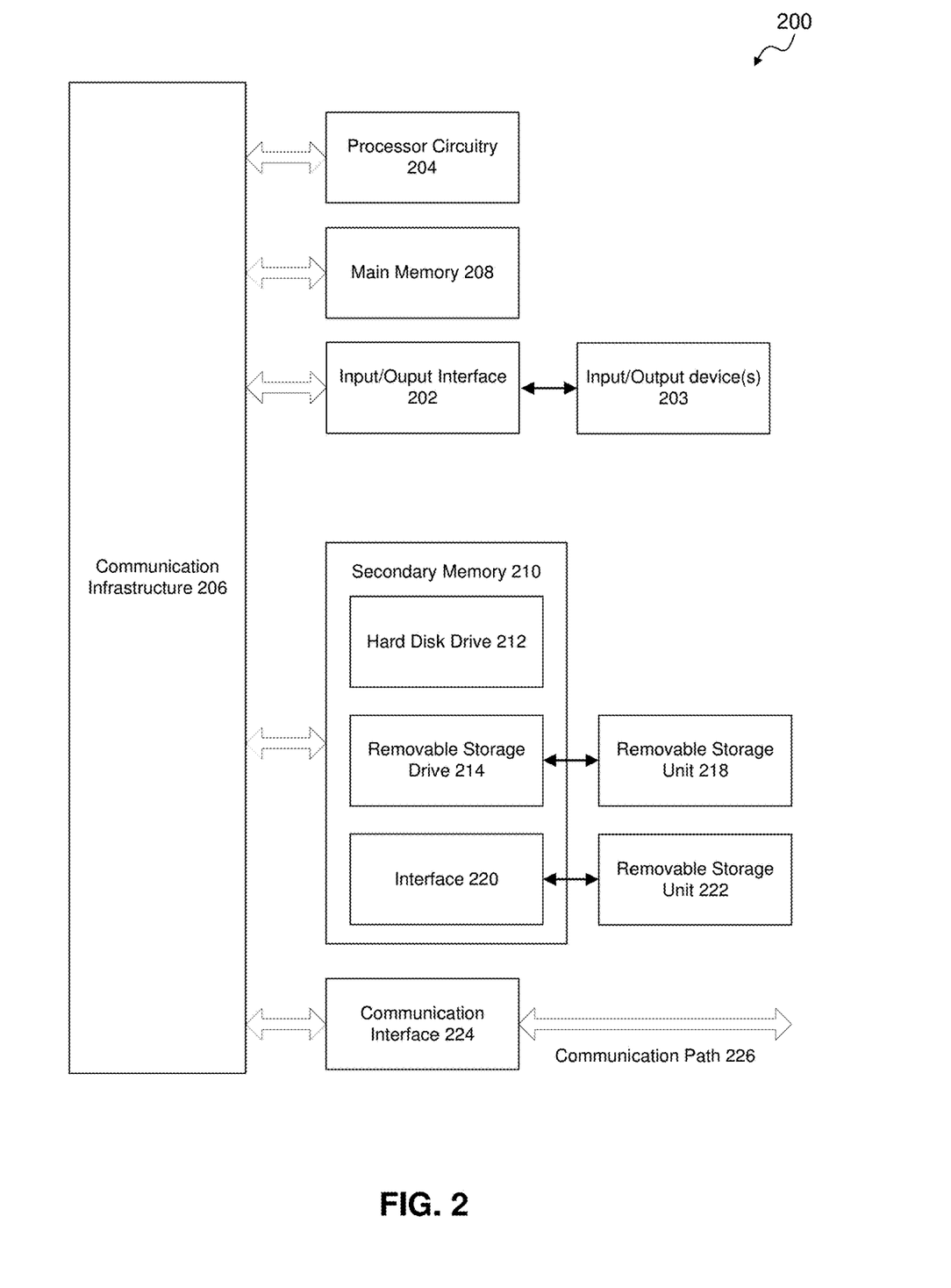
FIG. 2 is a block diagram of an alpha angle measurement system in accordance with an exemplary embodiment of the present disclosure.

FIG. 2 illustrates an anatomical angle measurement system 200 according to an exemplary embodiment. In an exemplary aspect, the system 200 is an embodiment of terminal 13 shown in FIG. 1. In an alternative aspect, the anatomical angle measurement system 200 is an embodiment of the terminal 13, the image processor 17, and/or system computer 20.

In an exemplary embodiment, system 200 includes processor circuitry 204 connected to a communication infrastructure or bus 206. The processor circuitry 204 may include one or more processors (also called central processing units, or CPUs). One or more of the processors may be a graphics processing unit (GPU). In an embodiment, a GPU is a processor that is a specialized electronic circuit designed to rapidly process mathematically intensive applications on electronic devices. The GPU may have a highly parallel structure that is efficient for parallel processing of large blocks of data, such as mathematically intensive data common to computer graphics applications, images and videos.

System 200 also includes user input/output device(s) 203, such as monitors, keyboards, pointing devices, etc., which communicate with communication infrastructure 206 through user input/output interface(s) 202.

System 200 also includes a main or primary memory 208, such as random access memory (RAM). Main memory 208 may include one or more levels of cache. Main memory 208 has stored therein control logic (i.e., computer software) and/or data, that when executed, control the system 200 to perform the operations of the system 200, such as determining one or more alpha angle measurements.

System 200 may also include one or more secondary storage devices or memory 210. Secondary memory 210 may include, for example, a hard disk drive 212 and/or a removable storage device or drive 214. Removable storage drive 214 may be a floppy disk drive, a magnetic tape drive, a compact disk drive, an optical storage device, tape backup device, and/or any other storage device/drive.

Removable storage drive 214 may interact with a removable storage unit 218. Removable storage unit 218 includes a computer usable or readable storage device having stored thereon computer software (control logic) and/or data. Removable storage unit 218 may be a floppy disk, magnetic tape, compact disk, DVD, optical storage disk, flash memory device and/or any other computer data storage device. Removable storage drive 214 reads from and/or writes to removable storage unit 218 in a well-known manner According to an exemplary embodiment, secondary memory 210 may include other means, instrumentalities or other approaches for allowing computer programs and/or other instructions and/or data to be accessed by system 200. Such means, instrumentalities or other approaches may include, for example, a removable storage unit 222 and an interface 220. Examples of the removable storage unit 222 and the interface 220 may include a removable memory chip (such as an EPROM or PROM) and associated socket, a memory stick and USB port, a memory card and associated memory card slot, and/or any other removable storage unit and associated interface.

System 200 may further include a communication or network interface 224. Communication interface 224 enables system 200 to communicate and interact with any combination of remote devices, remote networks, remote entities, etc. For example, communication interface 224 may allow system 200 to communicate with remote devices over communications path 226, which may be wired and/or wireless, and which may include any combination of LANs, WANs, the Internet, etc. Control logic and/or data may be transmitted to and from system 200 via communication path 226.

In an exemplary aspect, the communication interface 224 is configured to interface with the magnetic resonance apparatus 5, including with one or more components of the magnetic resonance apparatus 5. For example, the system 200 may acquire or otherwise receive information and/or data from the magnetic resonance apparatus 5 (e.g. magnetic resonance scanner S and/or controller 10) that is used by the system 200 to determine one or more alpha angle measurements. In an exemplary aspect, the system 200 receives the following information or data: (1) MR image data; (2) MR image data and radial slices; (3) MR image data and 3D segmentation of bones; or MR image data, 3D segmentation of bones, and given radial slices. In an exemplary embodiment, the system 200 is a special purpose computer configured to determine one or more alpha angle measurements according to the aspects of the present disclosure.

In an exemplary embodiment, to determine alpha angle measurements, the system 200 generates a three-dimensional (3D) bone surface image of the bone joint based on two-dimensional (2D) segmentations on radial plane slices of the bone joint, estimates, based on the 3D bone surface image, a head center of a head of the bone joint and a neck axis of a neck of the bone joint, constructs an alpha angle model based on the estimated head center and neck axis, and determines the alpha angle measurement for each of the radial plane slices of the bone joint based on the constructed alpha angle model. In an exemplary embodiment, the bone joint is a femoral head-neck junction of the hip.

The exemplary operations of the anatomical angle measurement system 200 will be described in further detail with references to FIGS. 3-6.

In an exemplary embodiment, the system 200 (e.g. processor circuitry 204) is configured to obtain MR image data using the magnetic resonance apparatus 5. For example, the terminal 13 may receive MR image data from the controller 10 and scanner S. In embodiments where the controller 10 is configured to perform the anatomical angle measurements, the controller 10 can receive signals, data, and/or other information from the scanner S, which is then processed by the controller 10 to determine the angle measurement(s).

Based on the MR image data, the system 200 is configured to estimate the axis of the neck 303 (FIG. 3), which is referred to as the neck axis. The neck axis is the normal of the plane 314, which is shown in projection by the blue line in FIG. 3. In this example, the neck axis extends along the Y-axis shown in FIG. 3. In an exemplary embodiment, the estimation of the neck axis can use one or more pattern recognition algorithms and/or artificial intelligence, such as an automatic landmark detection and image registration engines (e.g. ALPHA: Automatic Landmarking and Parsing of Human Anatomy).

Based estimated neck axis, the system 200 is configured to generate radial plane slices of the bone joint to form radial slice groups including the radial plane slices. In an exemplary embodiment, the system 200 can receive radial slices as an input in addition to the MR image data. In this aspect, the neck axis is computed from the radial slices instead of through landmarking and the radial slice group(s) is formed from the given radial slices.

In an exemplary embodiment, the system 200 is configured to generate one or more two-dimensional (2D) segmentations based on the radial slices. In an exemplary embodiment, the system 200 is configured to convolute each of the radial plane slices using a convolutional network to obtain bone boundary information of the radial plane slices. Distance constraint information of the bone boundary information is then regressed using a regression network to generate spatial information of the radial plane slices. As discussed in more detail below, the 3D bone surface image is generated based on the spatial information of the radial plane slices. In an exemplary embodiment, a fully convolutional network (e.g. Y-net) is used to generate the segmentation on 2D radial slices.

Figure 6:
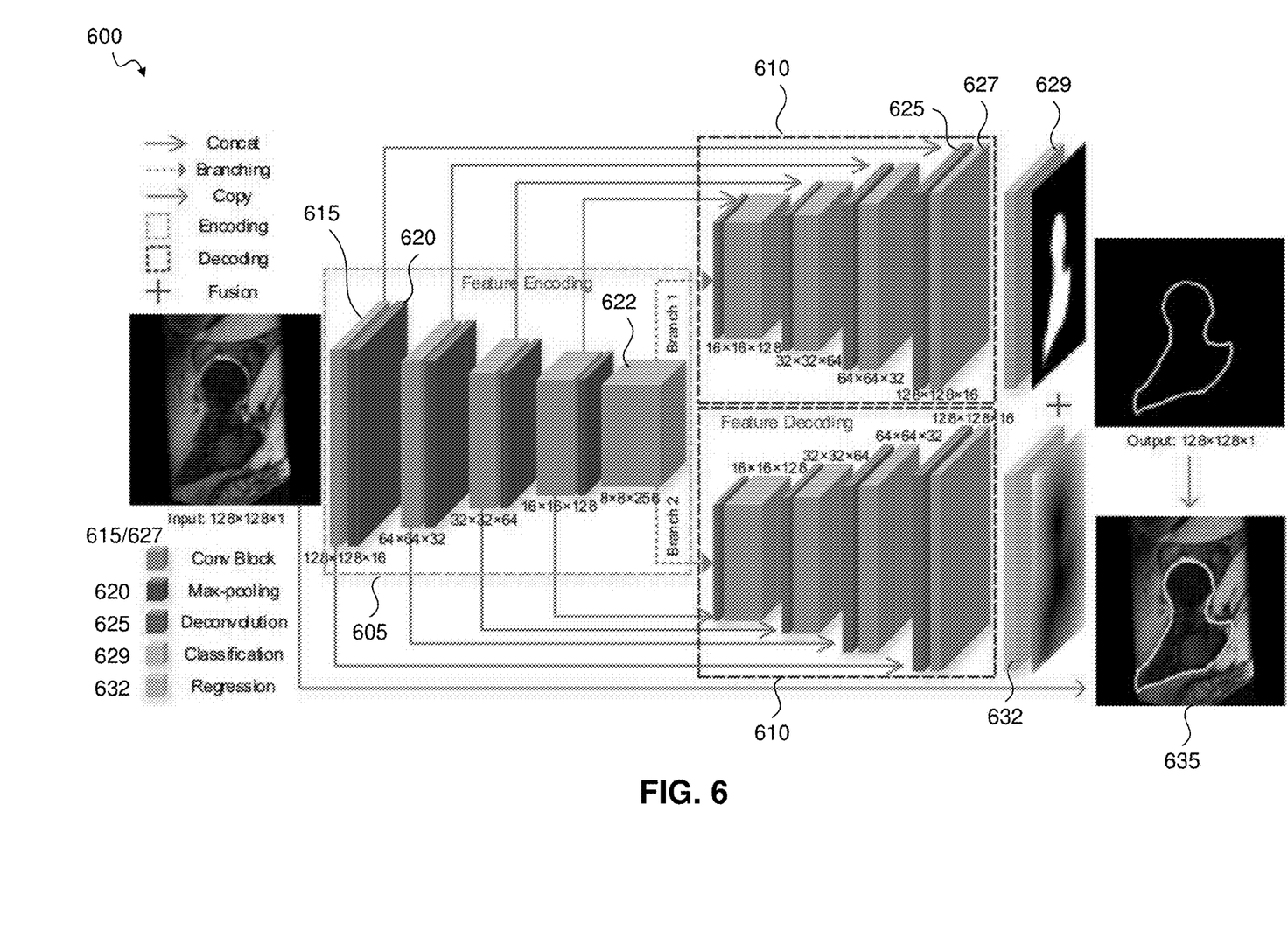
FIG. 6 illustrates the 2D segmentation operation in accordance with an exemplary embodiment of the present disclosure.

FIG. 6 illustrates the 2D segmentation operation 600 on the radial slices according to an exemplary embodiment. In an exemplary embodiment, the organ segmentation is formulated as a multi-task network that includes two parallel end-to-end branches. In this example, each task involves two symmetrical parts: encoding 605 and decoding 610. In an exemplary embodiment, the first task is a fully convolutional network configured for the inference of organ probability map (branch 1), and the second task is a deep regression network (DRN) that regresses the distance constraint information of organic boundary (branch 2). In an exemplary embodiment, during the distance regressing, the DRN produces continuously numerical constraints of spatial information. Advantageously, the DRN provides an increased potential to preserve the smoothness of the boundary as compared to the discrete classified labels obtained by boundary classification.

As shown in FIG. 6, the encoding bock 605 is configured to encode to abstract multi-level contextual features. The encoding block 605 includes four pairs that each include convolutional block 615 and max-pooling block 620. The encoding block 605 further includes a convolutional block 622 that provides two outputs to the first and second branches. In an exemplary embodiment, each convolution block 615 (blue) includes two convolutional layers with filter size of 3×3 and zero-padding of 1.

The decoding blocks 610 include four pairs that each include deconvolutional block 625 followed by a convolutional block 627. The output of the decoding block 610 of branch 1 is provided to a classification block 629 that provides discrete classified labels obtained by boundary classification.

The output of the decoding block 610 of branch 2 is provided to a regression block 632 that is a DRN configured to regresses the distance constraint information of the organic boundary to produce continuously numerical constraints of spatial information. In an exemplary embodiment, the boundary classification information from branch 1 is combined with the spatial information from branch 2 to produce the 2D segmentation on the radial slices 635. In an exemplary embodiment, the convolutional blocks (615, 627) and deconvolutional blocks 625 include parametric rectified linear unit and batch normalization.

In an exemplary embodiment, the system 200 is configured to generate a 3D surface of the bone based on the 2D segmentation of the radial slices. In an exemplary embodiment, the system 200 is configured to compute the boundary of the bone in each 2D radial slice and reconstruct the 3D bone surface based on the computed bone boundaries of the respective radial slices.

In an exemplary embodiment, the estimation of the neck axis using pattern recognition algorithm(s), such as ALPHA provides a rough estimate of the neck axis. In this example, the 3D bone surface is segmented from surface to surface of: the bone (e.g. femur) head, the surface of the femur neck, and the remaining portions of the femur. From this bone surface segmentation, an accurate shape fitting is performed to determine the femur head center and radius with the surface of the femur head, and the femur neck axis with the surface of the neck.

In an exemplary embodiment, based on the 3D bone surface, the system 200 is configured to finely estimate a head center 304 ($C_{head}$) of the head 302 of the bone joint and a neck axis of a neck 303 of the bone joint. The neck axis is the normal of the plane 314, which is shown in projection by the blue line in FIG. 3. In this example, the neck axis extends along the Y-axis shown in FIG. 3.

In an exemplary embodiment, the system 200 is configured to perform a rough surface segmentation on the 3D bone surface based on the surface generated based on 3D segmentation, which includes as an input to the system 200: ($P_{surface}$, $E_{surface}$, $F_{surface}$) vertices, edges and faces (triangles); the bone (femur) head center ($p_{head}$); and neck center ($p_{neck}$). Based on this information, the system 200 is configured to determine the head surface $P_{HEAD}$ based on the following equation:

$$P_{NECK} = \{p \mid p \in P_{surface} \text{ and } \angle p_{head} p_{neck} p < \frac{\pi}{3}\}$$

The system 200 is configured to determine the neck surface $P_{NECK}$ as follows:

$$P_{NECK} = \left\{p \mid p \in P_{surface} \text{ and} -0.8 < \frac{uv}{|u||v|} < 0.8, u = \overline{p_{head} p_{neck}}, v = \overline{p_{neck} p}\right\}$$

$E_{NECK} \subset E_{surface}$, $F_{NECK} \subset F_{surface}$ based on $P_{NECK}$ where ($P_{NECK}$, $E_{NECK}$, $F_{NECK}$) is a surface with two openings of the neck, similar with a one-sheet hyperboloid.

Figure 5:
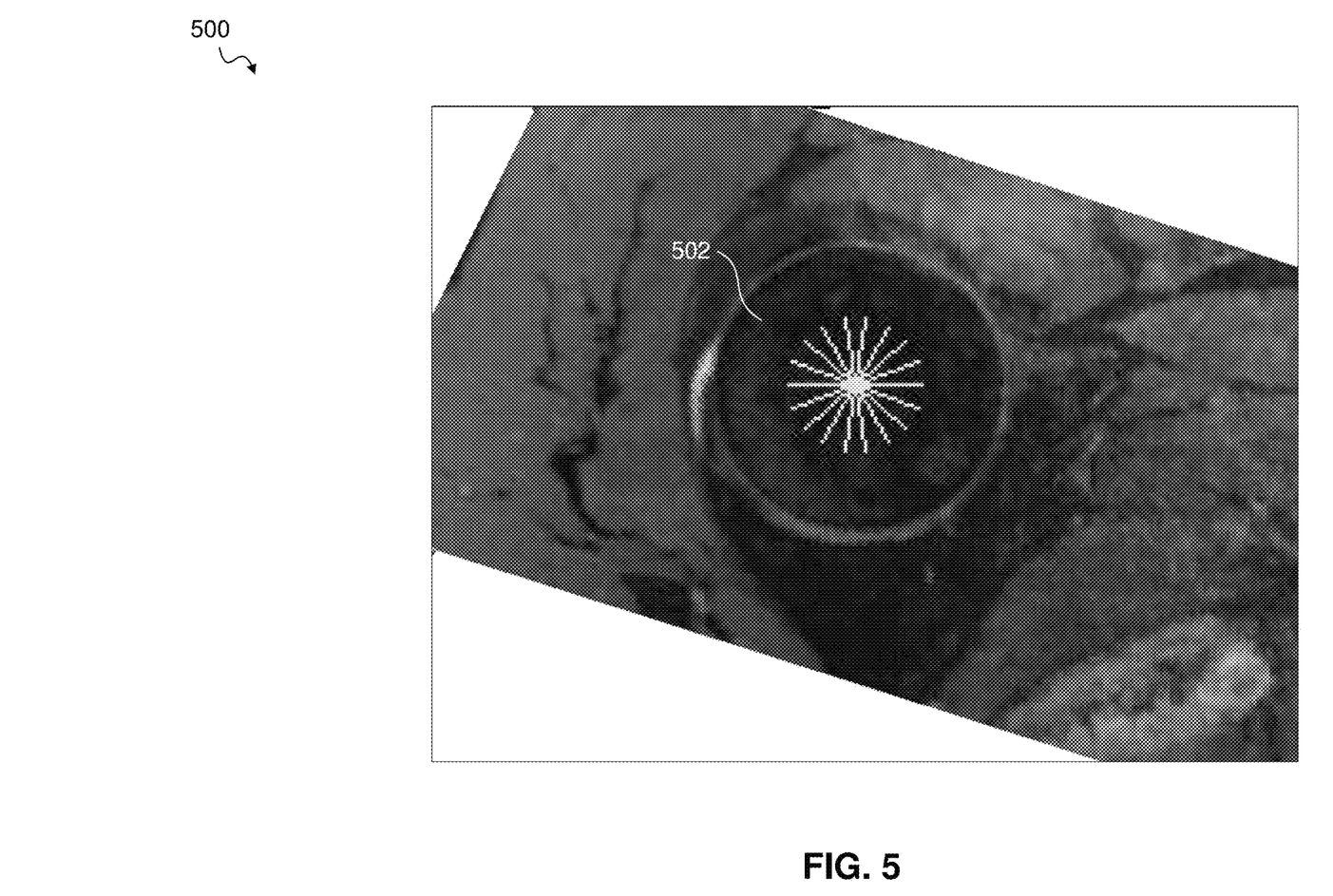
FIG. 5 is an illustration of a head center construction in accordance with an exemplary embodiment of the present disclosure.

In an exemplary embodiment, with reference to FIG. 5, the system 200 is configured to estimate the head center and head radius of the head 502 (302 in FIG. 3) using an iterative estimation process. In an exemplary embodiment, the system 200 is configured to estimate the head center and head radius using random sample consensus (RANSAC) algorithm. In this example, the system 200 performs sphere fitting using RANSAC, including randomly selecting a plurality of points (e.g. 4 points) on the femur head surface $P_{HEAD}$. Using these points, the sphere parameters (center and radius) are estimated. The inliers are then counted as an indicator of the accuracy of the selection and estimation. The selection, estimations and counting of inliers is repeated until the number of inliers. Sphere parameters are then estimated based on the iteration that satisfies the threshold (e.g. the optimal sphere with the most inliers).

Figure 3:
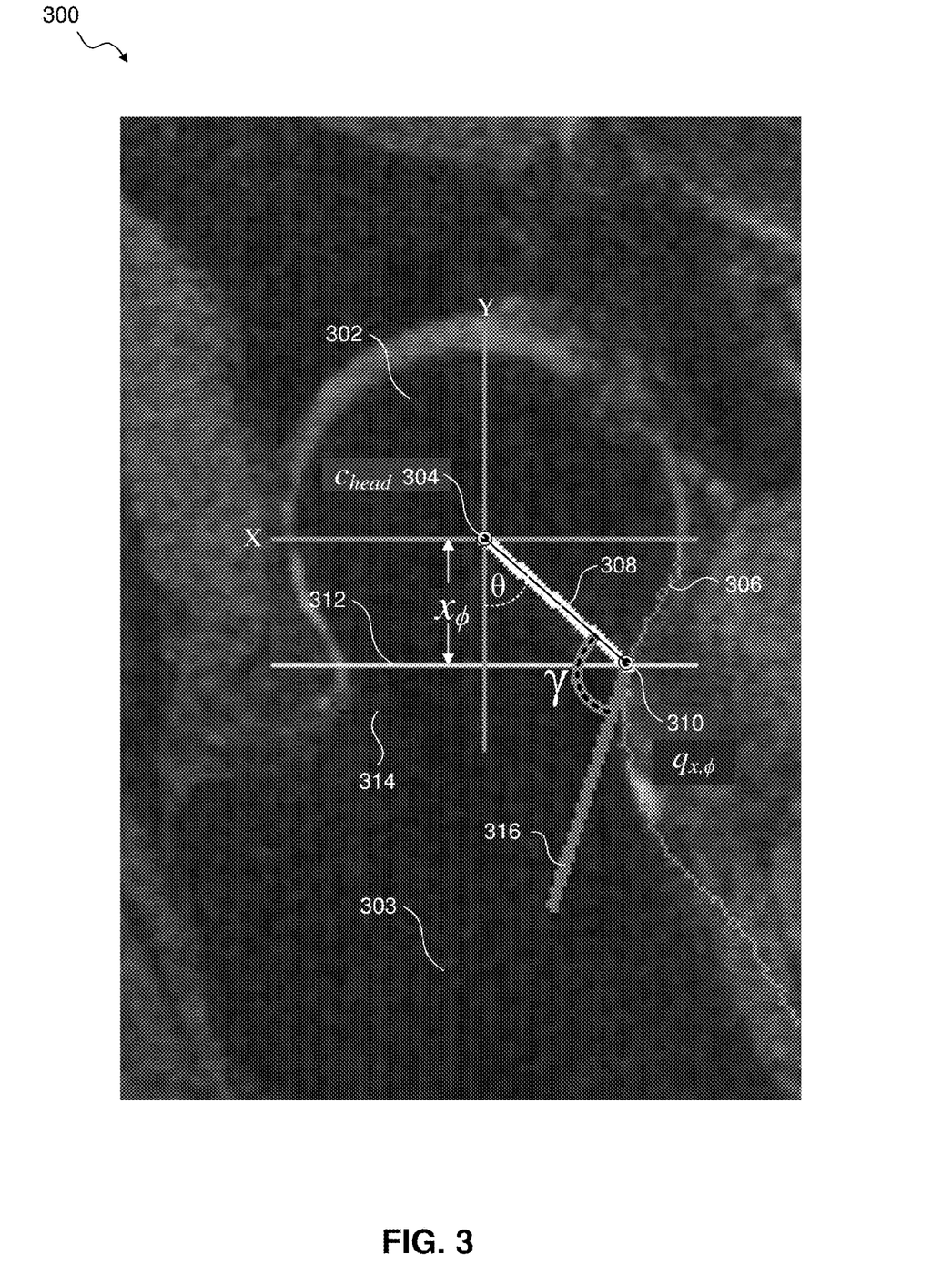
FIG. 3 is an illustration of an alpha angle measurement construction in accordance with an exemplary embodiment of the present disclosure.

In an exemplary embodiment, the system 200 is configured to estimate the neck axis orientation by determining a circle around the neck ($S_{NECK}$) of the bone joint having a smallest diameter. In an exemplary embodiment, the circle around the neck ($S_{NECK}$) is determined based on the following:

$$S_{NECK} = (P_{NECK}, E_{NECK}, F_{NECK})$$

where ($P_{NECK}$, $E_{NECK}$, $F_{NECK}$) is a surface with two openings of the neck, similar with a one-sheet hyperboloid. In an exemplary embodiment, the circle $S_{NECK}$ around the bone includes a circle on the undirected graph $G_{NECK} = (P_{NECK}, E_{NECK})$, where any path between the two openings intersect with the circle. The system 200 then fits a plane (314 in FIG. 3) to the circle, where the plane's normal is the femur neck axis orientation (Y-axis in FIG. 3. As shown in FIG. 3, the neck axis goes through the head center 304.

In an exemplary embodiment, based on the determined head center ($p_{head}$) and neck center ($p_{neck}$), the system 200 is configured to construct an alpha angle model for each degree $\phi$ with the head center 304 and neck axis 314. In this example, $\phi$ is the radial azimuth angle defining the radial plane slice. In an exemplary embodiment, the construction of the alpha angle model is based on the estimated head center 304 and neck axis 314.

In an exemplary embodiment, as shown in FIG. 3, to constructing the alpha angle model, the system 200 is configured to determining a bone boundary 306 of the bone joint, and angle ($\gamma_{x,\phi}$) between a line 308 (white line) defined from the head center 304 to the determined bone boundary 306 and a tangent line 316 (purple line) at the bone boundary 306. A projection of the line 308 on the neck axis (Y-axis) defines a center offset distance ($x_\phi$). A line 312 (yellow line) that extends from the intersection 310 ($q_{x,\phi}$) of the line 308 and the bone boundary 306 to the neck axis defines the center offset distance ($x_\phi$). In an exemplary embodiment, the determination of the bone boundary, angle ($\gamma$), and the center offset distance ($x_\phi$) are performed for each radial plane slice.

With reference to FIG. 3, the system 200 is configured to compute the following parameters on each radial slice:
a. the femur head center $c_{head}$ and radius $r_{head}$
b. $x_\phi$: the distance of the femur head center 304 to the yellow horizontal line 312
c. $q_{x,\phi}$: the intersection 310 of the yellow line 312 and the bone boundary 306.
d.

$$R_{x,\phi} = \frac{c_{head} q_{x,\phi}}{r_{head}}$$

e. $\theta_{x,\phi}$: the angle between the line 308 (e.g. line $c_{head} q_{x,\phi}$) and the vertical green line on the radial slice (Y-axis)

f. $\gamma_{x,\phi}$: the angle between line 308 (e.g. line $c_{head}q_{x,\phi}$) and the tangent line 316 of the bone boundary 306 (red curve) at the intersection 310 ($q_{x,\phi}$)

Again, $\phi$ is the radial position (azimuth angle) of the radial slice, and the neck axis (Y-axis) direction is determined by fitting a plane, who's normal is the neck axis direction. The blue line 314 in FIG. 3 is the projection of plane.

Figure 4:
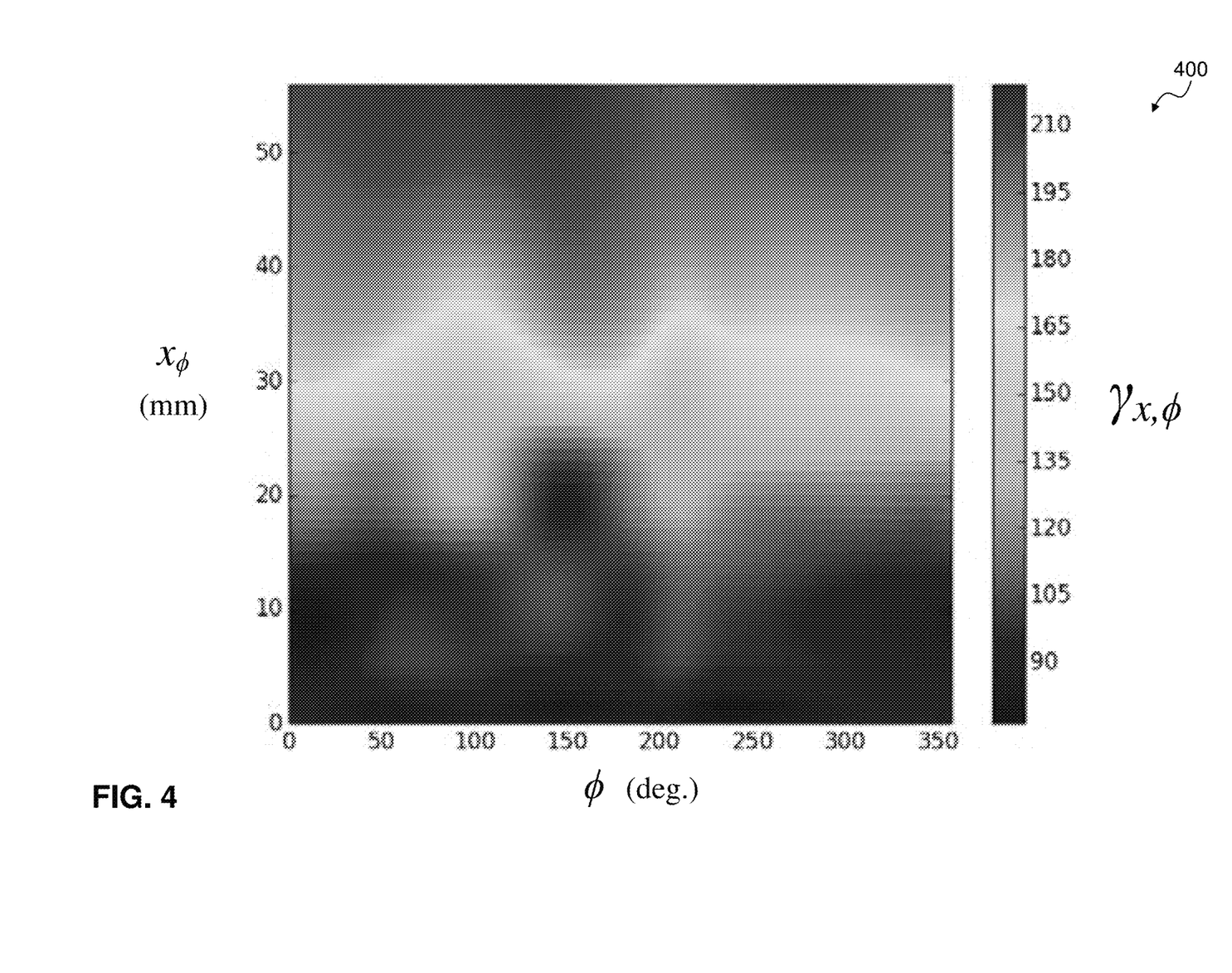
FIG. 4 is map of alpha angle measurement parameters in accordance with an exemplary embodiment of the present disclosure.

Based on the determined parameters, the system 200 may construct a 2D map 400 for the angle ($\gamma_{x,\phi}$) based on the center offset distance ($x_\phi$) and $\phi$ as shown in FIG. 4.

In an exemplary embodiment, the system 200 is configured to determine an optimized center offset distance based on the respective angles ($\gamma_{x,o}$) from each of the radial plane slices. In an embodiment, the optimized center offset distance $x_\phi'$ is determined based on a loss function. In an exemplary embodiment, the optimized center offset distance $x_\phi'$ is determined based on the loss function:

$$\operatorname{argmin}_x \sum_{\phi=0}^{n-1} \left( (\gamma_{x_\phi,\phi} - \gamma 0)^2 + \beta_1(\gamma_{x_\phi-1,\phi} - \gamma_{x_\phi+1,\phi}) + \beta_2 Dis(\theta_{x_\phi,\phi}, \theta_{x_\phi,(\phi+1)\%n}) \right)$$

Where:

$\gamma 0$ is the target value of $\gamma$. In an embodiment, the empirical default value of $\gamma 0$ is 120°, but is not limited thereto;

n is the number of radial slices, which can be adjusted based on, for example, a user input;

$\beta_1$ and $\beta_2$ are balance parameters to balance the objective function. In an embodiment, $\beta_1 = 1/3$, and $\beta_2 = 1/0.45$, but are not limited thereto;

$\tau$ is the maximum value of alpha angle difference between neighboring slices. In an embodiment, $$= 1.3 \times \frac{360}{n},$$

but is not limited thereto; and $$Dis(a,b) = \begin{cases} (a-b)^2, & |a-b| < \tau \\ \inf, & \text{otherwise} \end{cases}.$$

In this example, the term that is weighted with $\beta_1$ ensures that gamma is getting larger around this point. The term weighted with $\beta_2$ is a smoothness constraint, preventing unreasonably large jumps between the alpha angles of neighboring slices, but allowing flexibility for irregular shapes in diseased patients as well.

In an exemplary embodiment, the system 200 is configured to determine the alpha angle measurement for each of the radial plane slices of the bone joint based on the constructed alpha angle model. For example, the constructed alpha angle model is used to determine the optimized center offset distance $x_\phi'$, and the optimized center offset distance $x_\phi'$ is used to calculate the alpha angle measurement for each radial plane slice. With reference to FIG. 3, in this example, the alpha angle measurement for each radial plane slice is calculated by determining the intersection point 310 of the bone boundary 306 that corresponds to the optimized center offset distance $x_\phi'$. Using adjusted intersection point 310, the respective alpha angle is determined by determining the angle between the neck axis (Y-axis) and the line 308 connecting the head center 304 and the bone boundary point 310. In an exemplary embodiment, system 200 is configured to automatically quantify a joint function, such as to diagnose one or medical conditions (e.g. femoroacetabular impingement (FAI)).

In an exemplary embodiment, an image is generated of the respective alpha angles, which can be displayed, for example, on the display 14 of terminal 11. In an exemplary, the computed alpha angles are displayed in a Cartesian or radial fashion in 2D or color coded on a 3D bone model.

Figure 7:
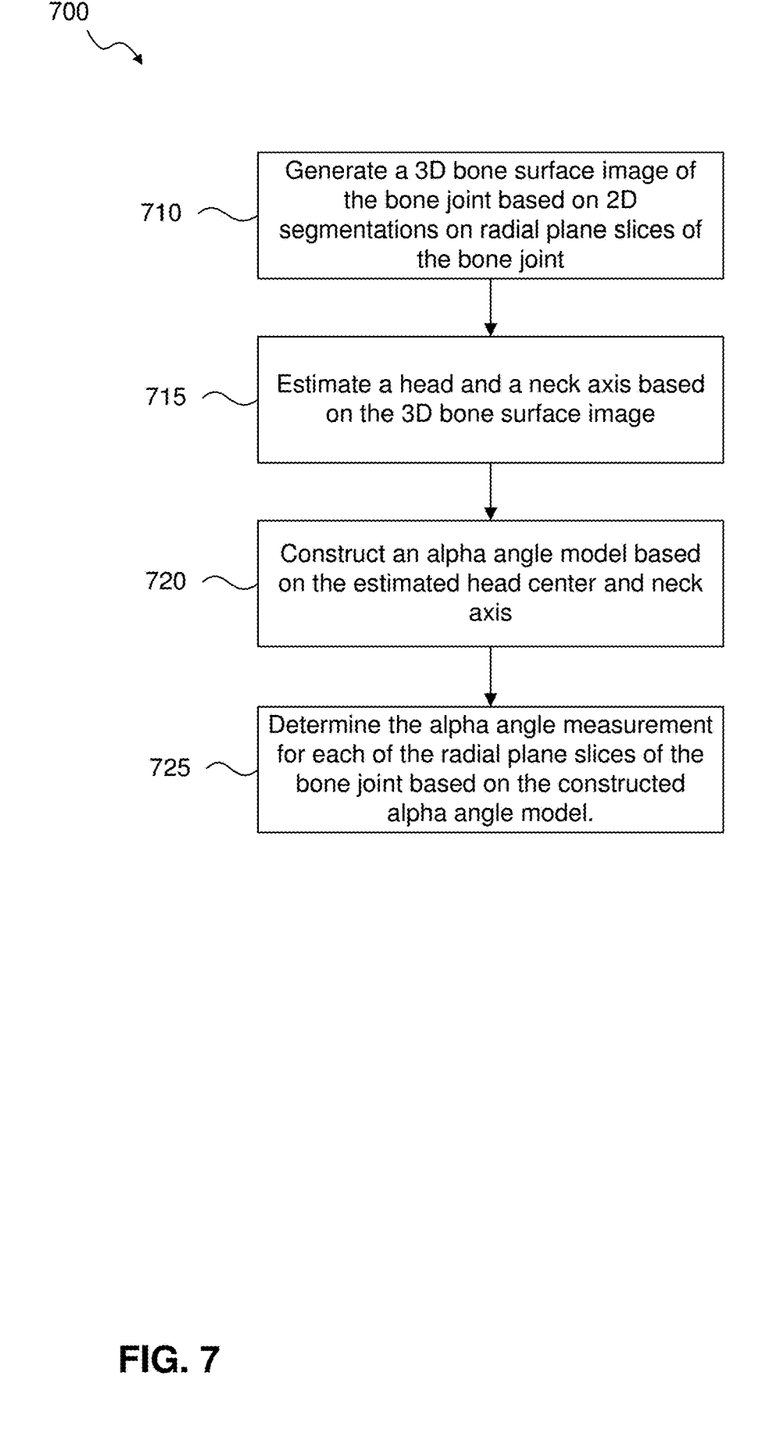
FIG. 7 illustrates a flowchart of a method an alpha angle measurement calculation method according to an exemplary embodiment of the present disclosure.

FIG. 7 illustrates a flowchart 700 of a method an alpha angle measurement calculation method according to an exemplary aspect of the present disclosure. The flowchart 700 may be a computer-implemented method executed by and/or otherwise associated with one or more processors and/or storage devices. These processors and/or storage device may be, for instance, associated with the system 200 and/or apparatus 5. In an aspect, flowchart 700 may be performed via one or more processors (e.g., those associated with the system 200 as shown in FIG. 2) executing instructions stored on a suitable storage medium (e.g., a non-transitory computer-readable storage medium). The flowchart 700 is described with continued reference to FIGS. 1-6. The operations are not limited to the order described below, and the various operations may be performed in a different order. Further, two or more operations of the methods may be performed simultaneously with each other. Aspects may include alternate or additional steps that are not shown in FIG. 7 for purposes of brevity.

The method of flowchart 700 begins at operation 710, where a three-dimensional (3D) bone surface image of the bone joint is generated based on two-dimensional (2D) segmentations on radial plane slices of the bone joint.

After operation 710, the flowchart 700 transitions to operation 715, where, based on the 3D bone surface image, a head center of a head of the bone joint and a neck axis of a neck of the bone joint are estimated.

After operation 715, the flowchart 700 transitions to operation 720, where an alpha angle model is constructed based on the estimated head center and neck axis.

After operation 720, the flowchart 700 transitions to operation 725, where the alpha angle measurement for each of the radial plane slices of the bone joint is determined based on the constructed alpha angle model (e.g. optimized center offset distance $x_\phi'$).

CONCLUSION

The aforementioned description of the specific embodiments will so fully reveal the general nature of the disclosure that others can, by applying knowledge within the skill of the art, readily modify and/or adapt for various applications such specific embodiments, without undue experimentation, and without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general purpose computer.

For the purposes of this discussion, the term "processor circuitry" shall be understood to be circuit(s), processor(s), logic, or a combination thereof. A circuit includes an analog circuit, a digital circuit, state machine logic, other structural electronic hardware, or a combination thereof. A processor includes a microprocessor, a digital signal processor (DSP), central processing unit (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

What is claimed is:

1. A method for alpha angle measurements of a bone joint based on magnetic resonance imaging (MRI) data of the bone joint, comprising:

generating a three-dimensional (3D) bone surface image of the bone joint based on two-dimensional (2D) segmentations on radial plane slices of the bone joint;

estimating, based on the 3D bone surface image, a head center of a head of the bone joint and a neck axis of a neck of the bone joint;

constructing an alpha angle model based on the estimated head center and neck axis; and determining the alpha angle measurement for each of the radial plane slices of the bone joint based on the constructed alpha angle model.

2. The method of claim 1, further comprising:

generating a radial slice group including the radial plane slices of the bone joint based on pattern recognition of characteristics of the bone joint.

3. The method of claim 2, further comprising:

performing 2D segmentation of the radial plane slices of the radial slice group to generate the 2D segmentations of the radial plane slices.

4. The method of claim 2, wherein the 2D segmentation of the radial plane slices of the radial slice group comprises:

convoluting each of the radial plane slices using a convolutional network to obtain bone boundary information of the radial plane slices; and regressing distance constraint information of the bone boundary information using a regression network to generate spatial information of the radial plane slices.

5. The method of claim 4, wherein the generation of the 3D bone surface image is based on the spatial information of the radial plane slices.

6. The method of claim 1, wherein the generation of the 3D bone surface image is based on a bone boundary for each of the radial plane slices of the bone joint.

7. The method of claim 2, wherein the pattern recognition of the characteristics of the bone joint comprises performing an automatic landmark detection on the MRI data.

8. The method of claim 1, wherein estimating the head center comprises:

roughly segmenting the 3D bone surface image to generate a bone head surface and a bone neck surface; and performing a random sample consensus on the bone head surface to estimate sphere parameters of a sphere to fit the sphere on the head of the bone joint, the head center corresponding to a center of the sphere.

9. The method of claim 1, wherein estimating the neck axis comprises:

determining a circle around the neck of the bone joint having a smallest diameter; and fitting a plane for the circle, wherein a normal of the plane is the neck axis.

10. The method of claim 1, wherein constructing the alpha angle model comprises constructing the alpha angle model for each radial plane slice of the radial plane slices based on the estimated head center and neck axis, each radial plane slice being defined by a radial azimuth angle.

11. The method of claim 1, wherein constructing the alpha angle model comprises:

for each radial plane slice of the radial plane slices:
determining a bone boundary of the bone joint; and
determining an angle ($\gamma$) between a line defined from the head center to the determined bone boundary and a tangent line at the bone boundary, a projection of the line on the neck axis defining a center offset distance (x); and determining, using a loss function, an optimized center offset distance based on the determined angles ($\gamma$) from each of the respective radial plane slices.

12. The method of claim 11, wherein determining the alpha angle measurement comprises, for each radial plane slice of the radial plane slices:
 determining an adjusted bone boundary of the bone joint based on the respective optimized center offset distance; and
 determining an alpha angle between a line defined from the head center to the adjusted bone boundary and the neck axis.

13. The method of claim 1, further comprising:
 displaying an output image representative of the alpha angle measurement for each of the radial plane slices.

14. The method of claim 13, wherein displaying an output image representative comprises:
 overlaying the output image representative on the 3D bone surface image.

15. The method of claim 13, wherein the bone joint is a femoral head-neck junction.

16. A non-transitory computer-readable storage medium with an executable program stored thereon, wherein, when executed, the program instructs a processor to perform the method of claim 1.

17. An anatomical angle measurement system to determine alpha angle measurements of a bone joint based on magnetic resonance imaging (MRI) data of the bone joint, comprising:
 a storage medium configured to store program instructions; and
 processor circuitry configured execute the program instructions to:
  generate a three-dimensional (3D) bone surface image of the bone joint based on two-dimensional (2D) segmentations on radial plane slices of the bone joint;
  estimate, based on the 3D bone surface image, a head center of a head of the bone joint and a neck axis of a neck of the bone joint;
  construct an alpha angle model based on the estimated head center and neck axis; and
  determine the alpha angle measurement for each of the radial plane slices of the bone joint based on the constructed alpha angle model.

18. The system of claim 17, wherein the 2D segmentation comprises:
 convoluting each of the radial plane slices using a convolutional network to obtain bone boundary information of the radial plane slices; and
 regressing distance constraint information of the bone boundary information using a regression network to generate spatial information of the radial plane slices.

19. The system of claim 17, wherein:
 estimating the head center comprises:
  roughly segmenting the 3D bone surface image to generate a bone head surface and a bone neck surface; and
  performing a random sample consensus on the bone head surface to estimate sphere parameters of a sphere to fit the sphere on the head of the bone joint, the head center corresponding to a center of the sphere; and
 estimating the neck axis comprises:
  determining a circle around the neck of the bone joint having a smallest diameter; and
  fitting a plane for the circle, wherein a normal of the plane is the neck axis.

20. The system of claim 17, wherein constructing the alpha angle model comprises:
 for each radial plane slice of the radial plane slices:
  determining a bone boundary of the bone joint; and
  determining an angle ($\gamma$) between a line defined from the head center to the determined bone boundary and a tangent line at the bone boundary, a projection of the line on the neck axis defining a center offset distance (x); and
 determining, using a loss function, an optimized center offset distance based on the determined angles ($\gamma$) from each of the respective radial plane slices, wherein alpha angle measurement is determined based on the optimized center offset distance.

* * * * *